(12) United States Patent
Mundrick et al.

(10) Patent No.: US 6,637,429 B2
(45) Date of Patent: Oct. 28, 2003

(54) PEDIATRIC ABDOMINAL SUPPORT

(76) Inventors: Annette M. Mundrick, 7523 Epaulet La., Maumee, OH (US) 43537; Barbara M. Stengle, 2443 Meadowwood, Toledo, OH (US) 43606

( * ) Notice: Subject to any disclaimer, the term of this patent is extended or adjusted under 35 U.S.C. 154(b) by 0 days.

(21) Appl. No.: 09/992,650

(22) Filed: Nov. 16, 2001

(65) Prior Publication Data

US 2002/0059931 A1 May 23, 2002

Related U.S. Application Data

(60) Provisional application No. 60/249,976, filed on Nov. 20, 2000.

(51) Int. Cl.$^7$ ................................................. A61F 5/24
(52) U.S. Cl. .................... 128/96.1; 128/845; 128/869; 128/876; 602/19
(58) Field of Search ................................ 128/845, 869, 128/875, 876; 602/5, 19

(56) References Cited

U.S. PATENT DOCUMENTS

| 1,751,595 | A | * | 3/1930 | Nachman | |
|---|---|---|---|---|---|
| 3,817,245 | A | * | 6/1974 | Kroeger | 128/134 |
| 4,396,013 | A | * | 8/1983 | Hasslinger | 128/134 |
| 5,492,496 | A | * | 2/1996 | Walker | 602/19 |
| 5,518,009 | A | * | 5/1996 | Ruiz-Gonzalez | 128/876 XZ |

* cited by examiner

Primary Examiner—Michael A. Brown
(74) Attorney, Agent, or Firm—MacMillan, Sobanski & Todd; Donald R. Fraser

(57) ABSTRACT

An abdominal support for a pediatric patent is described wherein the support includes an elongate strip of knit elastic material having an extended surface and a length sufficient to surround the torso of a pediatric patient in the region of the abdomen. Separable fastening elements are provided to selectively and adjustably fasten the ends of the strip together to snugly fit the patient. A fabric sleeve is provided to receive the major portion of the length of the strip to functionally reside in use between the one surface of the strip and the patient at operational rates.

7 Claims, 1 Drawing Sheet

PEDIATRIC ABDOMINAL SUPPORT

This application claims the benefit of U.S. provisional patent application Ser. No. 60/249,976, filed Nov. 20, 2000.

BACKGROUND OF THE INVENTION

1. Field of the Invention

The present invention relates to surgical devices and more particularly to a controlled release therapeutic device or system for the treatment of infants by a therapeutic device which includes dynamic structural means therein to controllably dispense a body treating material to the infant over a prolonged period of time by the slow release of body treating material.

2. Description of the Prior Art

Baclofen (Lioresal) is a drug that is widely used for patients with spasticity of muscles. Spasticity is a tightness or stiffness of muscles which typically results from a disorder or injury to the central nervous system. Presently, it is believed that damage to the brain or spinal cord may prevent certain nerve signals from reaching areas of the spinal cord that normally releases a substance; namely, gamma-aminobutyric acid (GABA). GABA is an amino acid which functions as an inhibitory calming neurotransmitter and plays a role in muscle relaxation. Baclofen is similar to GABA and functions as a muscle relaxant and antispastic. Typically, Baclofen is administered orally or intrathecally.

Intrathecal Baclofen therapy is a unique treatment for spasticity. The therapy delivers Baclofen directly into the fluid surrounding the spinal cord in small, precisely controlled doses using a pump that is implanted internally of the patient. If the drug is administered intrathecally, the pump is implanted in the abdomen of the patient and a catheter in the form of a long hollow plastic tube is inserted into the patient's intrathecal space where the medication can be pumped directly into the spinal fluid by the pump. The Baclofen medication pump is about one-inch thick and measures three inches in width and weighs about six ounces.

After the pump and the catheter are implanted surgically into the patient's abdomen, the surgeon uses an abdominal binder to decrease any possible surgical complications. The binder is used to prevent fluid retention around the pump, and decrease the possibility of the pump moving in the patient's abdomen. The binder increases the stability of the Baclofen pump in the "pump pocket" of the patient.

After pump placement in infants and small children, the prior practice has been to employ adult-sized binders and alter them to fit the children. It has been found that these binders were uncomfortable. Children patients complained of discomfort, irritation at incisional sites, and that some binders were too warm. The children did not like wearing the altered adult binders and parents were not motivated to encourage the children to wear them.

The above problems led to the development of a pediatric abdominal binder containing the features of the present invention.

It is an object of the invention to produce a surgical device for use by infants to assist in maintaining a controlled release therapeutic device in the abdomen of a pediatric patient.

Another object of the invention is to produce a surgical device for use with pediatric patients to apply pressure to an operative site adjacent an implanted structural means to controllably dispense a body treating material.

The above objects may typically be achieved by producing an abdominal support for a pediatric patient comprising an elongate strip of elastic material having an extended surface and spaced apart ends of a length sufficient to surround the patient in the region of the abdomen of the patient; separable fasteners attached to the ends of the strip for accommodating patients of differing girths; and a cover disposed adjacent at least the extended surface of the strip adapted to lay against the abdomen of the patient.

BRIEF DESCRIPTION OF THE DRAWINGS

The above as well as other objects and advantages of the invention will become readily apparent to those skilled in the art from reading the following detailed description of the invention when considered in the light of the accompanying drawings, in which.

DETAILED DESCRIPTION OF THE PREFERRED EMBODIMENT

Figure 1:
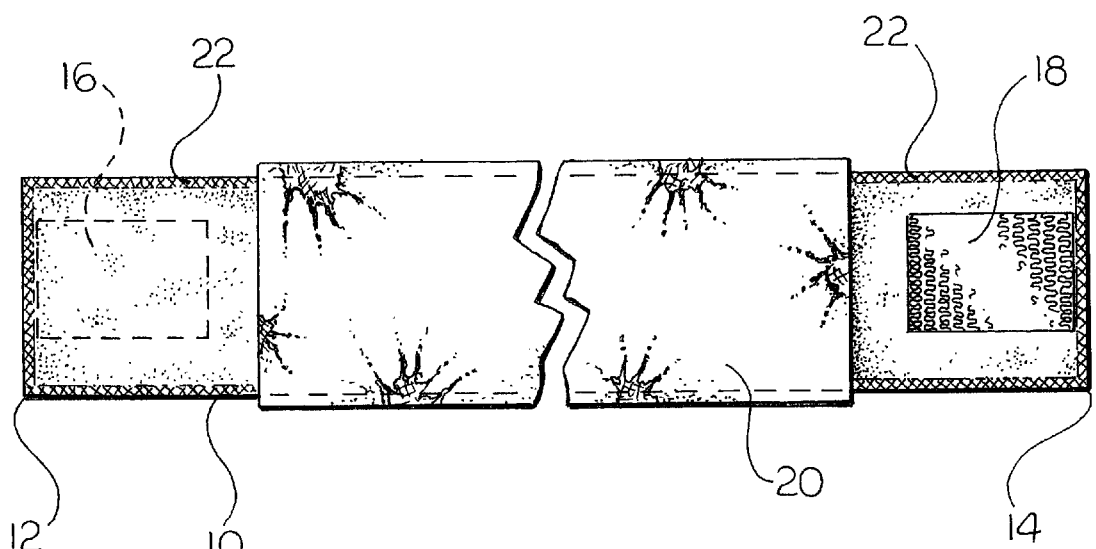
FIG. 1 is a top plan view of a pediatric abdomen binder incorporating the features of the invention.
Figure 2:
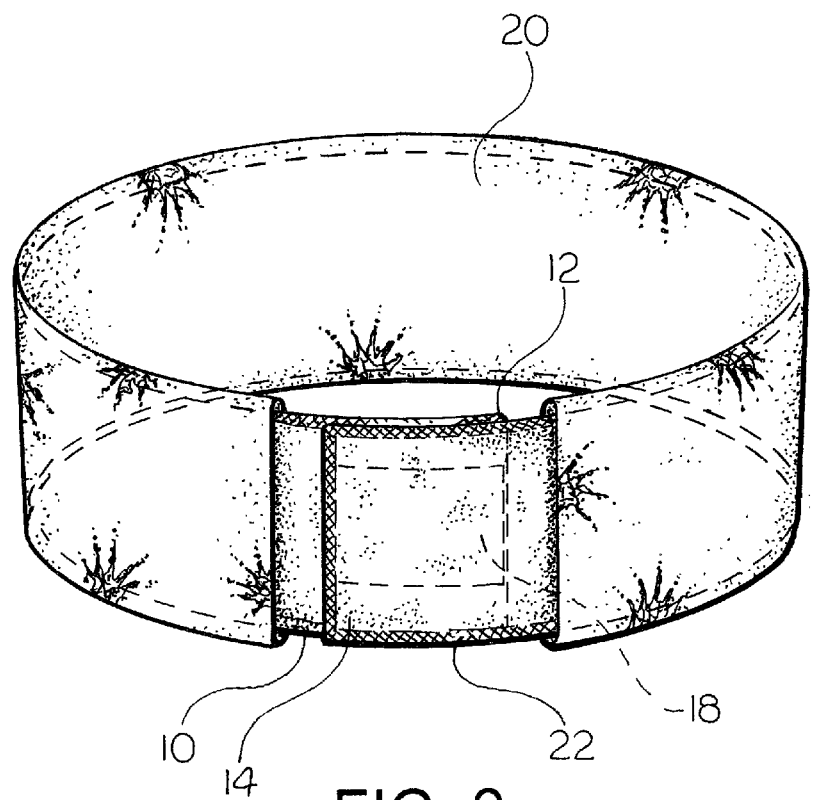
FIG. 2 is a perspective view of binder illustrated in FIG. 1 wherein the opposite ends are fastened together.

Referring to the accompanying drawings, there is illustrated a pediatric abdominal support containing the features of the instant invention. More specifically, FIGS. 1 and 2 illustrate an abdominal support for use with pediatric patients which includes a strip 10 having a first end 12 and a spaced apart second end 14. Typically, the strip 10 is formed of an elastic material of a width of from one-half (½) to six (6) inches wide and a length dependent upon the girth of the patient. Satisfactory results have been achieved by forming the strip 10 of a knit elastic material commercially available and sold and manufactured by South Carolina Elastic Co., Division of Rhode Island Textile Company.

The first end 12 of the strip 10 is provided with one section 16 of a separable fastener which is adapted to cooperate with another section 18 of a separable fastener. In the illustrated embodiment, Velcro fastener material was used and found to be completely satisfactory. It will be noted that the section 16 of Velcro tape is applied to the surface of the strip 10 which faces outwardly on the side opposite that which is intended to be facing the skin of the patient. The other section 18 of the Velcro tape is disposed at the opposite end 14 on the surface of the strip 10 designed to face inwardly toward the skin of the patient. The sections 16 and 18 of the Velcro tape may be secured to the respective surfaces of the strip 10 in any of the conventional manners such as, for example, by stitching.

The rather large area of Velcro tape used for the sections 16 and 18 permit the pressure applied by the overall binder structure to be easily and quickly changed. It has been found that the length of the sections 16 and 18 can typically fall into the range of from three (3) to four (4) inches. Other methods of securement of the sections 16 and 18 to the strip 10 include adhesive material, snap fasteners, or the like.

A removable sleeve 20 is disposed to cover the majority of the length of the strip 10. The sleeve 20 is formed of a fabric which presents an outer surface which is designed to be comfortable against the skin of the pediatric patient. The fabric from which the sleeve 20 is made also must be readily laundered.

It has been found that decorative cotton, cotton blend, or flannel fabrics possess the physical properties necessary to achieve the objectives of the binder. The width of the sleeve 20 is typically slightly larger than the width of the elastic strip 10; and the length of the sleeve 20 is approximately three fourths (¾) the length of the elastic strip 10.

While the sleeve 20 can be fabricated in a number of different forms, the preferred form includes a pair of single panels of fabric with the opposing edges being stitched together to form a sleeve to be fitted over the elastic strip 10, as illustrated.

Also, the preferred embodiment of the invention contains a decorative stitching 22 along the marginal edges of the elastic strip 10.

In use, the support described above is typically used to surround a pediatric patient's torso in the vicinity of operative incisions. More specifically, the support is to be used when there has been an incision to implant a pump and associated catheter in the patient. Typically, there are two incisional sites, one site is located in the lower abdomen and the other in the lumbar area of the back. In the past, these sites were covered with gauze, fleece or small fabric patches. It was difficult to adequately maintain the small squares underneath the old binders. The use of the above described binder having fabric sleeve 20 over the elastic strip 10 surprisingly overcame these difficulties. The utilization of the large area of Velcro tape sections 16 and 18 enables the level of pressure around the patient's abdomen to be varied when the patient is sitting or lying in different positions. The strip 10 of the binder is formed of sturdy elastic, which is easily washed, and has a long cycle of use. It will also be apparent that, if necessary, the fabric sleeve 20 may be laundered separately from the elastic strip 10. The size of the support can be customized to the size of the child and with a width and length that suits the patient perfectly. The supports may be colorful and attractive, and may be covered with a fabric sleeve 20 in a number of fun and colorful prints, and the edges may be surged to prevent raveling of the elastic.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. An abdominal support for a pediatric patient comprising:
   an elongate strip of elastic material having an extended surface and spaced apart ends and of a length sufficient to surround a pediatric patient in the region of the abdomen;
   separable fasteners attached to the ends of said strip for accommodating patients of differing girth; and
   a cover disposed adjacent at least the extended surface of said strip adapted to lay flat against the abdomen of the pediatric patient, wherein said strip is stretchable independent of said cover.

2. The invention defined in claim 1 wherein said strip is formed of an elastic web material.

3. The invention defined in claim 2 wherein said web material is of a knit fabric.

4. The invention defined in claim 1 wherein said fasteners are formed of hook and loop tape.

5. The invention defined in claim 1 wherein said cover is in the form of a sleeve.

6. The invention defined in claim 5 wherein said cover is formed of a fabric.

7. The invention defined in claim 6 wherein said fabric is flannel.

* * * * *